United States Patent [19]
Pearl

[11] Patent Number: 5,207,702
[45] Date of Patent: May 4, 1993

[54] METHOD AND APPARATUS FOR HANDLING HYGROSCOPIC DILATORS

[76] Inventor: Michael L. Pearl, 810 Sunrise Ct., Ann Arbor, Mich. 48103

[21] Appl. No.: 745,019

[22] Filed: Aug. 14, 1991

[51] Int. Cl.⁵ ............................................. A61B 17/28
[52] U.S. Cl. ...................................... 606/207; 81/418
[58] Field of Search ............... 606/142, 143, 205, 206, 606/207, 208, 209, 210, 211, 191, 192, 157; 81/424.5, 426.5, 418

[56] References Cited

U.S. PATENT DOCUMENTS

| | | | |
|---|---|---|---|
| 2,444,207 | 6/1948 | Smith | 606/207 |
| 4,192,313 | 3/1980 | Ogami | 128/321 |
| 4,411,259 | 10/1983 | Drummond | 606/207 |
| 4,480,642 | 11/1984 | Stoy et al. | 128/341 |
| 5,011,491 | 4/1991 | Boenko et al. | 81/418 |

FOREIGN PATENT DOCUMENTS 0020743  7/1905  Fed. Rep. of Germany ...... 606/207

*Primary Examiner*—C. Fred Rosenbaum
*Assistant Examiner*—William Lewis
*Attorney, Agent, or Firm*—John A. Bucher

[57] ABSTRACT

A method and apparatus for handling hygroscopic dilators having an elongated configuration with a rounded eyelet forming a hole at one end thereof, the method employing forceps having scissors-like members with opposed tips forming a rounded recess and an axially extending opening for securing the dilator in mating relation within the rounded recess, the tips having shoulders for gauging the depth to which the elongated dilator is to be inserted and grooved, generally flat surfaces surrounding the recess for facilitating retraction of the dilator.

13 Claims, 1 Drawing Sheet

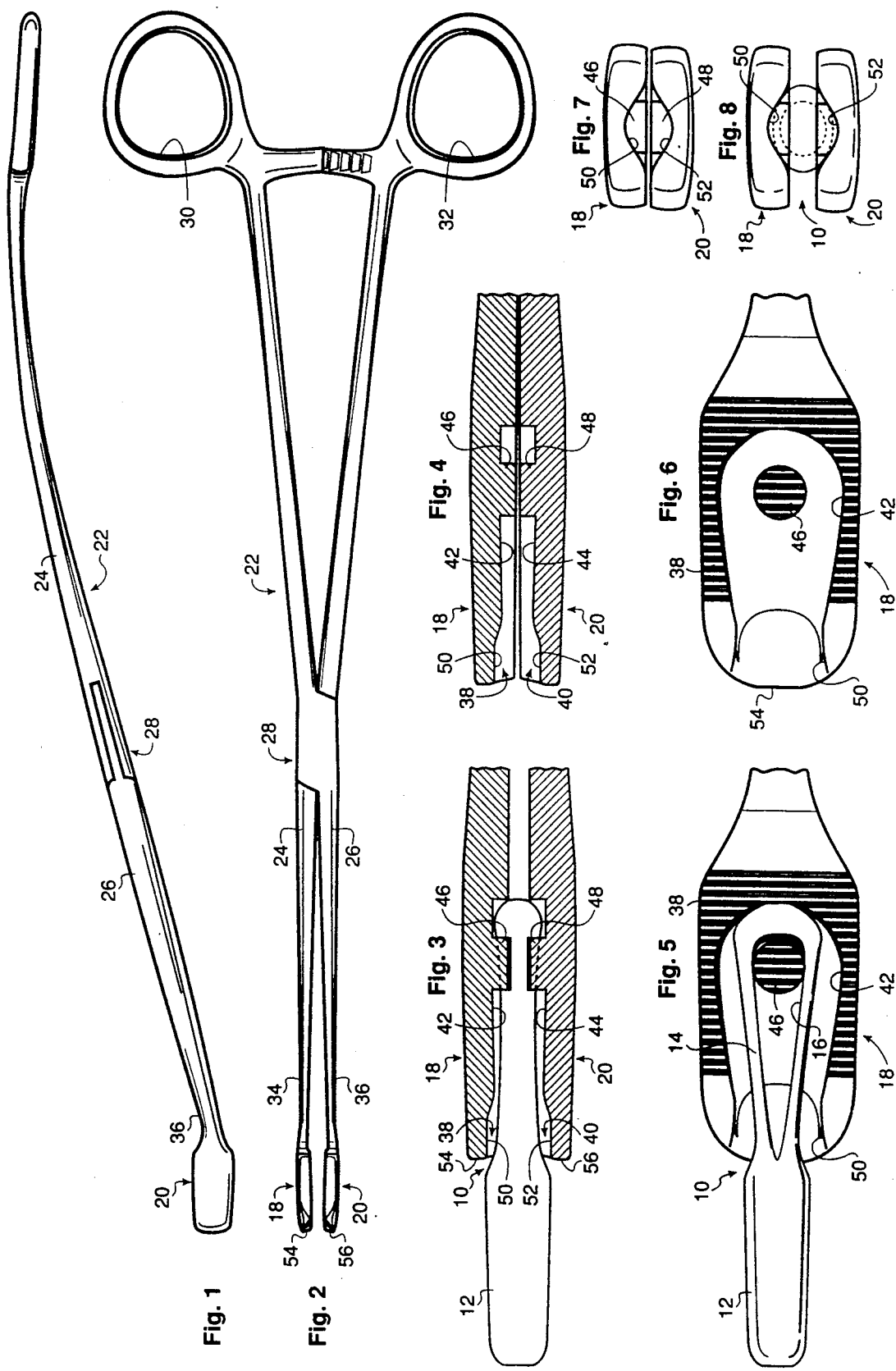

METHOD AND APPARATUS FOR HANDLING HYGROSCOPIC DILATORS

FIELD OF THE INVENTION

The invention relates to a method and apparatus for handling elongated hygroscopic dilators with a rounded eyelet forming a hole at one end thereof and more particularly to such a method and apparatus wherein the dilators are of synthetic composition.

BACKGROUND OF THE INVENTION

With increasing frequency, physicians need to gain access to the uterine cavity for such procedures as therapeutic abortion, insertion of intrauterine devices, and evaluation of the endometrium. Entry into the uterine cavity is via the uterine cervix, a fibromuscular organ intercalated between the vaginal vault and the uterus.

In its usual state, the cervical canal has a diameter of approximately 2-4 millimeters (mm.) which is too narrow to allow sufficient access. Traditionally, the cervical canal has been mechanically expanded with a series of sequentially graded metal rods. Although effective, the rods have several drawbacks including:

(1) considerable skill and experience are required for safe use;

(2) overly rapid dilation can lead to significant tissue trauma; and (3) they are painful, often requiring anesthesia prior to use.

The development of hygroscopic dilators has significantly reduced the need for rapid mechanical dilation of the cervical canal. An early example of a hygroscopic dilator was the Laminaria tent. This device is formed as a dry piece of seaweed root (*Laminaria japonica*) shaped generally like a large toothpick. When exposed to moisture, it gradually swells to several times its original diameter. This atraumatically and painlessly dilates the cervical canal.

More recently, a variation of such hygroscopic dilators was developed in the form of a dilator formed from a synthetic material such as a hydrogen exhibiting the necessary hygroscopic characteristics and available under the trade name "DILAPAN" from Gynotech, Inc., Lebanon, N.J. See U.S. Pat. No. 4,480,642 issued Nov. 6, 1984. Such synthetic dilators exhibited several advantages over Laminaria tents, including:

(1) the Laminaria tent inherently included small surface crevices rendering them incapable of complete sterilization; by contrast, synthetic dilators are entirely synthetic, allowing them to be completely sterilized;

(2) Laminaria tents inherently have rough surfaces which may cause tissue tearing upon insertion or removal; by contrast, synthetic dilators have smooth surfaces which reduce the risk of tissue tearing;

(3) the supply and price of organic raw materials from which Laminaria tents are produced fluctuate due to environmental factors; by contrast, synthetic dilators are produced by a synthetic process, leading to a stable supply and price;

(4) as Laminaria tents are hand crafted from a natural material, their initial diameter varies; by contrast, synthetic dilators are produced with close tolerances;

(5) Laminaria tents have a less uniform and relatively slower rate of swelling as compared to synthetic dilators.

Use of both types of hygroscopic dilators has become widespread throughout the United States. Because of the earlier availability of the Laminaria tent, it became more widely used. However, synthetic dilators are becoming more competitive with Laminaria tents for comparative reasons set forth above.

Both types of dilators are cylindrical. In contrast, the usual instruments employed in the past for insertion and removal of the dilators, for example, Bozeman uterine packing forceps and ring sponge clamps, have flat grasping surfaces. As a result, these instruments are unable to securely grasp the dilators. The resulting lack of control over the dilators by the manipulating forceps or the like may lead to several adverse consequences, including:

(1) an increased risk of perforation of the cervical or uterine tissue; and (2) the dilator must be discarded if it is accidentally dropped or contaminated, for example, by touching the vaginal walls, either occurrence tending to increase the expense of the dilators and associated procedures.

With the earlier developed Laminaria tent, forceps were developed for specifically facilitating insertion of the Laminaria tent into the uterine cervix, as set forth in U.S. Pat. No. 4,192,313 issued Mar. 11, 1980 to Ogami. The Ogami forceps were in the form of interconnected members having fore ends of the members including a plurality of elongated grooves forming edges for clamping onto the Laminaria tent to facilitate its insertion into the uterine cervix.

The Ogami forceps were superior to previously employed devices such as the Bozeman uterine packing forceps and ring sponge clamps because the inwardly tapered grooved surfaces of the Ogami forceps permitted improved clamping on the Laminaria tents. However, there was found to remain a need for further improvements in such forceps to further facilitate their use in inserting hygroscopic dilators into the cervical canal and preferably for also retracting the dilators when necessary.

SUMMARY OF THE INVENTION

It is accordingly an object of the invention to provide a method and apparatus for handling hygroscopic dilators, particularly of an elongated configuration with an eyelet at one end forming a hole extending through the dilator.

More specifically, it is an object of the invention to provide apparatus, useful in a corresponding method, in the form of tips arranged in opposed relation upon forceps or the like, the opposed tips forming together a rounded recess and an axially extending opening allowing the elongated dilator to extend from the tips with the rounded eyelet secured in generally mating relation within the rounded recess.

More particularly, it is an object of the invention to provide such a method and apparatus wherein the tips form pins means generally centered within the rounded recess and adapted for closing between the tips to extend through the hole of the rounded eyelet and thereby positively engage the elongated dilator within the tips.

It is an even further object of the invention to provide such a method and apparatus wherein the tips are formed with shoulders adjacent the axially extending opening for gauging the depth to which the elongated dilator is to be inserted before being released from the forceps.

It is yet a further object of the invention to provide such a method and apparatus wherein the tips have grooved, generally flat surfaces surrounding the rounded recess and axial opening for facilitating retraction of the elongated dilator when necessary.

Yet additional objects and advantages of the invention are apparent in the following description having reference to the accompanying drawings.

BRIEF DESCRIPTION OF THE DRAWINGS

FIG. 1 is a side view of forceps contemplated by the present invention with tips constructed according to the invention and arranged in opposed relation on the forceps.

FIG. 2 is a view taken from one side of FIG. 1 and including an edgewise or side view of the tips.

FIG. 3 is an enlarged fragmentary view, with parts in section, of the opposed tips having a hygroscopic dilator secured therebetween.

FIG. 4 is a similar enlarged fragmentary view of the tips urged into opposed relation and without the dilator arranged therebetween.

FIG. 5 is an interior plan view of one of the tips of FIG. 3 with the dilator in place.

FIG. 6 is similarly an interior plan view of one of the tips of FIG. 4 with the dilator removed.

FIG. 7 is a view taken from the left end of FIG. 4, as illustrated.

FIG. 8 is a view taken from the left end of FIG. 3, as illustrated, with the dilator secured between the tip.

Description of the Preferred Embodiment

Referring now to the drawings and particularly to FIGS. 3 and 5, the present invention relates to a method and apparatus for handling hygroscopic dilators such as that indicated at 10. The hygroscopic dilator 10 has an elongated configuration with a cylindrical end 12 formed from suitable synthetic hygroscopic material such as a hydrogel and adapted for insertion into a cervical canal as generally described above. The other end of the dilator is formed as an elongated eyelet 14 forming a hole 16.

In normal practice, it is contemplated that the dilator 10 be inserted into the cervical canal generally the length of the cylindrical end 12 so that the elongated eyelet 14 is left exposed or extending therefrom.

As noted above, insertion of the dilator 10 into the cervical canal is relatively simple in nature but still requires precise control in order to assure proper insertion of the dilator without damaging the surrounding tissue or causing pain or discomfort.

With prior art forceps such as the Ogami forceps referred to above, it was difficult to maintain proper alignment between the dilator and the forceps. Thus, the physician inserting the dilator could not be certain of desired alignment between the dilator and the forceps.

This problem and other disadvantages of the prior art are overcome by the method and apparatus of the present invention wherein opposed tips 18-20 are constructed according to the present invention and either integrally formed upon conventional forceps 22 or adapted for mounting thereon.

The forceps 22 are generally of a type including scissors-like members 24 and 26 which are hinged together at 28 and include respective finger holes 30 and 32 for manipulation.

The tips 18 and 20 are respectively mounted in opposed relation on the opposite ends 34 and 36 of the scissors-like members.

The interior surfaces 38 and 40 of the tips 18 and 20 are preferably of similar and symmetrical configuration. However, it will be apparent from the following description that certain features of the invention could be predominantly or entirely formed by one tip member or the other.

Referring particularly to FIGS. 5 and 6, the tips 18 and 20 from mating recessed openings 42 and 44 which, taken together, mate with the eyelet 14 of the dilator 10, at least when the dilator is secured between the tips as best illustrated in FIGS. 3 and 8.

The tips 18 and 20 also form mating pins 46 and 48 which are generally centered within the recessed openings 42, 44 and mate with each other so that they extend through the hole 16 in the eyelet 14 of the dilator 10 when the dilator is secured between the tips as illustrated. As noted above, it would of course be possible to form a pin on only one of the tips and to increase the length of the pin so that it would similarly extend through the hole of the dilator eyelet.

With the dilator properly positioned in the recessed openings 42, 44, the pins 46, 48 extend through the hole 16 in the eyelet in order to positively position the dilator between the tips so that a physician employing the forceps can rely upon the dilator being maintained in alignment generally as an extension of the opposite ends 34, 36 of the forceps.

The tips are also formed with axially extending openings 50 and 52 adapted for receiving the elongated eyelet 14 so that the cylindrical end 12 of the dilator can extend outwardly from the tips.

At the same time, the tips are formed with shoulders 54 and 56 generally adjacent and at the axial end of the openings 50 and 52. The shoulders 54 and 56 are dimensionally positioned relative to the recessed openings 42, 44 and the mating pins 46, 48 so that only the cylindrical end 12 of the dilator extends outwardly from the tips. Thus, a physician employing the forceps can use the shoulders 54, 56 as a gauge to determine the extent to which the dilator 10 is to be inserted into the cervical canal before it is released from between the tips. Thus, the tips 18, 20 constructed according to the present invention permit the forceps to properly and accurately position the dilator within the cervical canal and, moreover, to gauge the proper insertion of the dilator into the canal.

The interior surfaces 38 and 40 of the tips 18 and 20 are formed to be grooved and generally flat surrounding both the recessed openings 42, 44 and at least part of the axially extending openings 50 and 52.

Thus, when the forceps are employed to retract or remove the dilator after use or when necessary, the grooved, generally flat surfaces 38 and 40 facilitate engagement of the tips with the elongated eyelet 14 of the dilator even if the eyelet is not properly positioned within the recessed openings. Thus, the grooved, generally flat surfaces facilitate removal of the dilator if the physician is not readily able to properly align the tips with the dilator so that the elongated eyelet 14 is received within the recessed openings.

The method of the present invention is believed clearly apparent from the preceding description. However, the method is briefly described below in order to assure a complete understanding of the invention. Initially, in order to initiate a procedure for inserting the dilator 10 into a cervical canal, the tips 18, 20 for the forceps are formed as described above. The dilator 10 is then positioned so that its elongated eyelet 14 is secured in nested engagement between the recessed openings 42, 44 with the pins 46, 48 extending through the hole 16. Thus, the dilator 10 is positively positioned relative to the axis of the forceps permitting the physician to accurately insert the dilator into the cervical canal. The shoulders 54, 56 of the tips may be employed to gauge the proper depth of insertion for the dilator with the forceps then be disengaged from the dilator.

At the completion of the medical procedure or when otherwise necessary, the forceps may also be employed to retract or remove the dilator from the cervical canal. In that instance, the grooved, generally flat interior surfaces 38, 40 serve to facilitate engagement of the tips 18, 20 with the dilator even if its elongated eyelet 14 is not properly nested between the recessed openings. In either event, the design of the tips 18, 20 facilitates their engagement with the dilator 10 so that it can be readily removed from the cervical canal by the forceps.

There has accordingly been described a method and apparatus for facilitating manipulation of hygroscopic dilators in various medical procedures. Numerous modifications and variations, in addition to those specifically set forth above, will be apparent from the preceding description. Accordingly, the scope of the present invention is defined only by the following appended claims which are further exemplary of the invention.

What is claimed is:

1. Forceps for manipulating hygroscopic dilators having an elongated configuration with a rounded eyelet forming a hole at one end thereof, the forceps comprising scissors-like members having opposed tips respectively mounted thereon, the tips forming together a rounded recess and at least one of the tips forming pin means generally centered within the rounded recess and adapted for closing between the tips and extending through the hole of the rounded eyelet in order to positively engage the elongated dilator within the tips, the tips further forming an axially extending opening allowing the elongated dilator to extend from the tips.

2. The forceps of claim 1 wherein the pin means are partially formed by each tip.

3. The forceps of claim 1 wherein the tips have shoulders adjacent the axially extending opening, the shoulders being spaced apart from the rounded recess by a predetermined amount for gauging the depth to which the elongated dilator is to be inserted before it is released from the forceps.

4. The forceps of claim 3 wherein the tips have grooved, generally flat surfaces surrounding the rounded recess and axial opening for facilitating retraction of the elongated dilator.

5. The forceps of claim 1 wherein the tips have grooved, generally flat surfaces surrounding the rounded recess and axial opening for facilitating reaction of the elongated dilator.

6. The forceps of claim 1 wherein the tips are integrally formed with the respective scissors-like members.

7. A pair of tips adapted for mounting in opposed relation on scissors-like members of forceps for manipulating hydroscopic dilators having an elongated configuration with a rounded eyelet forming a hole at one end thereof, the tips forming together a rounded recess and at least one of the tips forming pin means generally centered within the rounded recess and adapted for closing between the tips and extending through the hole of the rounded eyelet in order to positively engage the elongated dilator within the tips, the tips further forming an axially extending opening allowing the enlogated dilator to extend from the tips.

8. The tip pair of claim 7 wherein the tips have shoulders adjacent the axially extending opening, the shoulders being spaced apart from the rounded recess by a predetermined amount for gauging the depth to which the enlogated dilator is to be inserted before it is released from the forceps.

9. The tip pair of claim 8 wherein the tips have grooved, generally flat surfaces surrounding the rounded recess and axial opening for facilitating reaction of the elongated dilator.

10. The tip pair of claim 7 wherein the tips have grooved, generally flat surface surrounding the rounded recess and axial opening for facilitating reaction of the elongated dilator.

11. A method for inserting a hydroscopic dilator having an elongated configuration with a rounded eyelet forming a hole at one end thereof into a cervical canal, comprising the steps of providing opposed tips on scissors-like members of forceps, the tips forming together a rounded recess and at least one of the tips forming pin means generally centered within the rounded recess and adapted for closing between the tips and extending through the hole of the rounded eyelet in order to positively engage the elongated dilator within the tips, the tips further forming an axially extending opening allowing the elongated dilator to extend from the tips as the enlogated dilator is inserted into the cervical canal, retaining the elongated dilator in secured engagement within the tips and inserting it into the cervical canal, and then releasing the elongated dilator from the tips and leaving the elongated dilator in place within the cervical canal.

12. The method of claim 11 wherein the tips have shoulders adjacent the axially extending opening, the shoulders being spaced apart from the rounded recess by a predetermined amount for gauging the depth to which the elongated dilator is to be inserted it is released from the forceps.

13. The method of claim 11 wherein the tips have grooved, generally flat surfaces surrounding the rounded recess and axial opening for facilitating reaction of the elongated dilator from the cervical canal.

* * * * *